United States Patent [19]

Ishimitsu et al.

[11] 4,316,044
[45] Feb. 16, 1982

[54] ISOVALERIC ACID DERIVATIVES

[75] Inventors: Keiichi Ishimitsu, Odawara; Isamu Kasahara, Ohiso; Tomio Yamada, Hiratsuka; Michihiko Matsuda, Ohiso; Hidemitsu Takahashi; Shuichi Soma, both of Hiratsuka, all of Japan

[73] Assignee: Nippon Soda Company Limited, Tokyo, Japan

[21] Appl. No.: 182,341

[22] Filed: Aug. 29, 1980

[30] Foreign Application Priority Data

Sep. 7, 1979 [JP] Japan .................................. 54-114235
Jan. 14, 1980 [JP] Japan .................................. 55-2897
Jan. 15, 1980 [JP] Japan .................................. 55-48745

[51] Int. Cl.$^3$ ........................ C07C 69/76; C07C 69/62; A61K 35/55
[52] U.S. Cl. ................................. 560/105; 560/20; 560/55; 560/100; 560/104; 560/219; 260/340.5 R; 260/465 D; 260/465 F; 564/305; 424/282; 424/305; 424/308; 424/309

[58] Field of Search .................. 560/105, 20, 55, 100, 560/104, 219; 260/465 D, 465 F; 424/282, 305, 308, 309

[56] References Cited

FOREIGN PATENT DOCUMENTS 359124 2/1962 Switzerland ........................ 560/105

Primary Examiner—Paul J. Killos

[57] ABSTRACT

Isovaleric acid derivatives having the formula

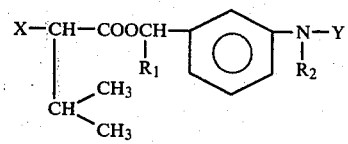

wherein typical representations of X is halophenyl, $R_1$ is hydrogen or cyano, $R_2$ is hydrogen or lower alkyl, and Y is halophenyl. These derivatives possess insecticidal and acaricidal properties. The process for their preparation is described.

10 Claims, No Drawings

ISOVALERIC ACID DERIVATIVES

DESCRIPTION

Background of the Invention

This invention relates to isovaleric acid derivatives having insecticidal and acaricidal properties, the method of preparation of these isovaleric acid derivatives and their use.

Brief Explanation of the Problem

For insecticidal having low order of toxicity to mammals, various synthetic pyrethroids have being developed. However, due to the high toxicity to fish, they have difficulty in their use as insecticides applicable in a waterfield rice plant. The present invention provides a compound which is as effective as synthetic pyrethroides, and far less toxic to fish.

Summary of the Invention

The novel compounds of the invention have the formula

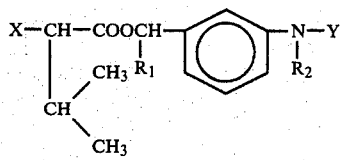
(I)

where X is phenyl substituted with halogen, lower alkyl, lower haloalkyl, lower haloalkoxy, 3,4-methylenedioxy or nitro group, naphthyl, styryl or lower alkenyl substituted with chlorine, $R_1$ is hydrogen, cyano or ethynyl, $R_2$ is hydrogen, lower alkyl, lower alkenyl or lower alkynyl, and Y is phenyl or halophenyl.

It is to be understood that the compounds of the present invention include isomers produced by assymmetric carbon atoms in the structural formula

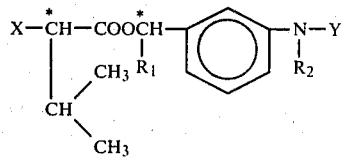

where X, Y, $R_1$ and $R_2$ have the above meaning, and * represents an assymmetric symbol.

DETAILED DESCRIPTION

The preparation of isovaleric acid derivatives of formula (I) comprises reacting isovaleric acid of the formula

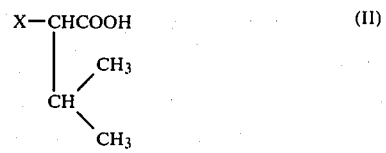
(II)

wherein X has the foregoing definition, with a benzyl alcohol of the formula

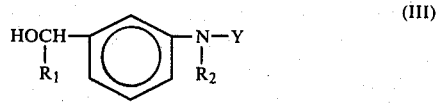
(III)

wherein $R_1$, $R_2$ and Y have the foregoing definitions. The reaction is usually carried out at room temperature in an inert solvent such as benzene, toluene and tetrahydrofuran, and in the presence of a basic catalyst as pyridine, triethylamine and sodium carbonate. Such reactive derivatives as an alkali-metal salt, lower alkyl ester or chloride of the compound of the formula (II) and chloride or bromide of the compound of the formula (III) are preferably used for the reaction. The compound of the formula (III) can be prepared, for example, in accordance with following reactions which illustrate where Y is 4-chlorophenyl.

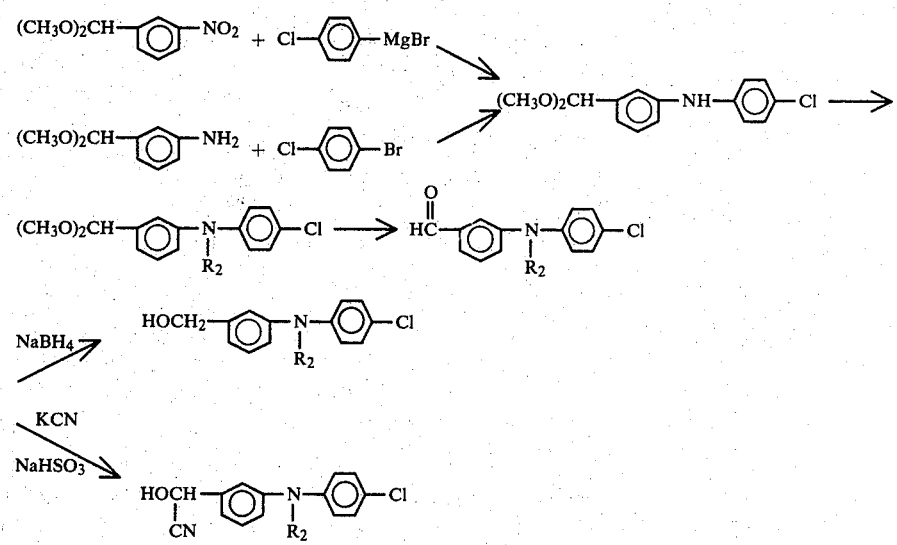

EXAMPLE 1

α-cyano-3-(4-chloroanilino)benzyl
α-isopropyl-4-chlorophenyl acetate

Into 40 ml of benzene were added 1.6 g of α-cyano-3-(4-chloroanilino)benzylalcohol and 1.0 g of pyridine. To this solution, 1.6 g of α-isopropyl-4-chlorophenyl acetylchloride was added dropwise under ice-cooling, and the mixture was stirred for about 12 hours at room temperature. The reaction mixture was then washed successively with 5% hydrochloric acid, 5% aqueous sodium carbonate solution and water, dried with magnesium sulfate, and evaporated. The oily residue was purified with a column chromatography to give 2.3 g of the desired compound.

EXAMPLE 2

3-(4-chloroamilino)benzyl α-isopropyl-4-chlorophenyl acetate

Into 25 ml of benzene were added 1.0 g of 3-(4-chloroanilino)benzylalcohol and 0.7 g of pyridine. To this solution, 1.0 g of α-isopropyl-4-chlorophenyl acetylchloride was added dropwise under ice-cooling, and the mixture was stirred for about 12 hours at room temperature. The reaction mixture was then washed successively with 5% hydrochloric acid, 5% aqueous sodium carbonate solution and water, dried with magnesium sulfate, and evaporated. The oily residue was purified with a column chromatography to give 1.2 g of the desired compound.

EXAMPLE 3

3-(N-methyl-4-chloroamilino)benzyl
α-isopropyl-4-chlorophenyl acetate

Into 20 ml of benzene were added 1.2 g of 3-(N-methyl-4-chloroamilino)benzylalcohol and 0.8 g of pyridine. To this solution, 1.1 g of α-isopropyl-4-chlorophenyl acetylchloride was added dropwise under ice-cooling, and the mixture was stirred for about 12 hours at room temperature. The reaction mixture was then washed successively with 5% hydrochloric acid, 5% aqueous sodium carbonate solution and water, dried with magnesium sulfate and evaporated. The oily residue was purified with a column chromatography to give 1.8 g of the desired compound.

EXAMPLE 4

α-cyano-3-(N-methyl-4-chloroanilino)benzyl
α-isopropyl-4-chlorophenyl acetate

Into 25 ml of benzene were added 1.2 g of 3-(N-methyl-4-chloroanilino)mandelonitrile and 0.7 g of pyridine. To the solution, 1.0 g of α-isopropyl-4-chlorophenyl acetylchloride was added dropwise under ice-cooling, and the mixture was stirred for about 12 hours at room temperature. The reaction mixture was then washed successively with 5% hydrochloric acid, 5% aqueous sodium carbonate solution and water, dried with magnesium sulfate and evaporated. The oily residue was purified with a column chromatography to give 1.3 g of the desired compound.

EXAMPLE 5

α-cyano-3-(N-n-propyl-4-chloroanilino)benzyl
α-isopropyl-4-chlorophenyl acetate

Into 20 ml of benzene were added 1.5 g of 3-(N-n-propyl-4-chloroanilino)mandelonitrile and 0.8 g of pyridine. To the solution, 1.1 g of α-isopropyl-4-chlorophenyl acetylchloride was added dropwise under cooling, and the mixture was stirred for about 12 hours at room temperature. The reaction mixture was then washed successively with 5% hydrochloric acid, 5% aqueous sodium carbonate solution and water, dried with magnesium sulfate and evaporated. The oily residue was purified with column chromatography to give 1.5 g of the desired compound.

EXAMPLE 6

α-cyano-3-(4-chloroanilino)benzyl
α-isopropyl-4-methoxyphenyl acetate

Into 20 ml of benzene were added 1.0 g of 3-(4-chloroanilino)mandelonitrile and 0.6 g of pyridine. To the solution, 0.9 g of α-isopropyl-4-methoxyphenyl acetylchloride was added dropwise under cooling, and the mixture was stirred for about 12 hours at room temperature. The reaction mixture was then washed successively with 5% hydrochloric acid, 5% aqueous sodium carbonate solution and water, dried with magnesium sulfate and evaporated. The oily residue was purified with a column chromatography to give 1.2 g of the desired compound.

EXAMPLE 7

α-ethynyl-3-(N-methyl-4-chloroanilino)benzyl
α-isopropyl-4-chlorophenyl acetate

Into 20 ml of benzene were added 0.8 g of α-ethynyl-3-(N-methyl-4-chloroanilino)benzylalcohol and 0.5 g of pyridine. To the solution, 0.7 g of α-isopropyl-4-chlorophenyl acetylchloride was added dropwise under cooling, and the mixture was stirred for about 12 hours at room temperature. The reaction mixture was then washed successively with 5% hydrochloric acid, 5% aqueous sodium carbonate solution and water, dried with magnesium sulfate and evaporated. The oily residue was purified with a column chromatography to give 0.8 g of the desired compound.

EXAMPLE 8

α-cyano-3-(4-chloroanilino)benzyl
(s)α-isopropyl-4-chlorophenyl acetate

Into 20 ml of benzene were added 1.3 g of 3-(4-chloroanilino)mandelonitrile and 0.8 g of pyridine. To the solution, 1.1 g of (s)(+)-α-isopropyl-4-chlorophenyl acetylchloride was added dropwise under cooling, and the mixture was stirred for about 12 hours at room temperature. The reaction mixture was then washed successively with 5% hydrochloric acid, 5% aqueous sodium carbonate solution and water, dried with magnesium sulfate and evaporated. The oily residue was purified with a solumn chromatography to give 1.5 g of the desired compound.

EXAMPLE 9

α-cyano-3-(4-chloroanilino)benzyl
α-isopropyl-2-naphthyl acetate

Into 20 ml of benzene were added 1.2 g of 3-(4-chloroanilino)mandelonitrile and 0.8 g of pyridine. To the solution, 1.2 g of α-isopropyl-2-naphthyl acethylchloride was added dropwise under cooling, and the mixture was stirred for about 12 hours at room temperature. The reaction mixture was then washed successively with a 5% hydrochloric acid, 5% aqueous sodium carbonate solution and water, dried with magnesium sulfate and evaporated. The oily residue was purified with a column chromatography to give 1.4 g of the desired compound.

Inclusive of the above examples, compounds within the scope of this invention which can be prepared in an analogous manner are shown on Table 1.

TABLE 1

$$X-CH(CH(CH_3)_2)-COOCH(R_1)-C_6H_4-N(R_2)-Y$$

| Compound No. | X | R₁ | R₂ | Y | Physical Properties | |
|---|---|---|---|---|---|---|
| 1 | Cl-C₆H₄- | H | H | C₆H₅ | $n_D^{30}$ | 1.6032 |
| 2 | " | " | " | 4-Cl-C₆H₄ | $n_D^{28}$ | 1.6122 |
| 3 | " | CN | " | C₆H₅ | $n_D^{23}$ | 1.6061 |
| 4 | " | " | " | 4-Cl-C₆H₄ | $n_D^{22}$ | 1.6075 |
| 5 | " | " | " | 2-Cl-C₆H₄ | $n_D^{26}$ | 1.6067 |
| 6 | " | " | " | 4-F-C₆H₄ | $n_D^{26}$ | 1.5927 |
| 7 | " | " | " | 2-Cl-C₆H₄ | $n_D^{34}$ | 1.5990 |
| 8 | " | " | " | 4-Br-C₆H₄ | $n_D^{33}$ | 1.6120 |
| 9 | " | H | CH₃ | 4-Cl-C₆H₄ | $n_D^{26}$ | 1.5910 |
| 10 | " | CN | " | " | $n_D^{32}$ | 1.5989 |
| 11 | " | H | " | 4-Br-C₆H₄ | $n_D^{30.5}$ | 1.6048 |
| 12 | " | CN | " | " | $n_D^{29}$ | 1.6022 |
| 13 | " | H | " | 4-F-C₆H₄ | $n_D^{25.5}$ | 1.5847 |
| 14 | " | CN | " | " | $n_D^{25.5}$ | 1.5817 |
| 15 | " | " | " | 2-Cl-C₆H₄ | $n_D^{23}$ | 1.5979 |
| 16 | " | H | C₂H₅ | 4-Cl-C₆H₄ | $n_D^{29.5}$ | 1.5863 |
| 17 | " | CN | " | " | $n_D^{29.5}$ | 1.5923 |
| 18 | " | " | ⁿC₃H₇ | " | $n_D^{26}$ | 1.5854 |
| 19 | " | H | ⁱC₃H₇ | " | $n_D^{21.5}$ | 1.5879 |
| 20 | " | CN | ⁱC₃H₇ | 4-Cl-C₆H₄ | $n_D^{22}$ | 1.5835 |
| 21 | " | H | ⁿC₄H₉ | " | $n_D^{21}$ | 1.5830 |
| 22 | " | CN | " | " | $n_D^{19.5}$ | 1.5896 |
| 23 | " | H | CH₂CH=CH₂ | " | $n_D^{21.5}$ | 1.5958 |
| 24 | " | CN | " | " | $n_D^{21}$ | 1.5912 |
| 25 | " | H | CH₂C≡CH | " | $n_D^{21.5}$ | 1.6007 |
| 26 | " | CN | " | " | $n_D^{24}$ | 1.5977 |
| 27 | " | C≡CH | CH₃ | " | $n_D^{20}$ | 1.5891 |
| 28 | ⁱC₄H₉-C₆H₄- | CN | H | " | $n_D^{20.5}$ | 1.5789 |

TABLE 1-continued $$X-CH-COOCH-\underset{R_1}{\underset{|}{C_6H_4}}-N\underset{R_2}{\overset{Y}{-}}$$
with CH(CH₃)₂ branch on the X-CH carbon (CH₃ and CH(CH₃)CH₃)

| Compound No. | X | R₁ | R₂ | Y | Physical Properties | |
|---|---|---|---|---|---|---|
| 29 | Br—C₆H₄— | " | " | " | $n_D^{22}$ | 1.6198 |
| 30 | F—C₆H₄— | " | " | " | $n_D^{22}$ | 1.5972 |
| 31 | CH₃—C₆H₄— | " | " | " | $n_D^{20}$ | 1.6005 |
| 32 | 2,4-Cl₂—C₆H₃— | " | " | " | $n_D^{22}$ | 1.6113 |
| 33 | methylenedioxyphenyl (O-CH₂-O-C₆H₃—) | " | " | " | $n_D^{22.5}$ | 1.6025 |
| 34 | CF₂HO—C₆H₄— | " | " | " | $n_D^{27}$ | 1.5830 |
| 35 | CH₃O—C₆H₄— | " | " | " | $n_D^{20}$ | 1.6068 |
| 36 | NO₂—C₆H₄— | " | " | " | $n_D^{25}$ | 1.6070 |
| 37 | Cl-C₆H₄— (ortho) | " | " | " | $n_D^{25}$ | 1.5969 |
| 38 | iC₃H₇—C₆H₄— | " | " | " | $n_D^{21}$ | 1.5827 |
| 39 | 2,3-Cl₂—C₆H₃— | " | " | " | $n_D^{21}$ | 1.6059 |
| 40 | CF₃—C₆H₄— (ortho) | " | " | " | $n_D^{20}$ | 1.5747 |
| 41 | naphthyl | " | " | " | | |
| 42 | C₆H₅—CH=CH— | " | " | " | $n_D^{18.5}$ | 1.6062 |
| 43 | Cl₂C=CHCH₂— | " | " | " | $n_D^{19}$ | 1.5902 |
| 44 | Cl₂C=CH— | " | " | " | $n_D^{15.5}$ | 1.6020 |

As already mentioned, the compounds of this invention exhibit outstanding insecticidal and acaricidal properties accompanied by the low toxicity to fish, so that the compounds are useful for controlling of various phytophagous insects and acarids. The insecticidal activity against the green rice leafhopper is unexpectedly high that the compounds are especially suitable for chemical control of a waterfield rice plant.

The compounds according to this invention are utilized, if desired, in a form of the usual pesticidal formulations with conventional diluents or extenders, and the formulations include wettable powders, granules, dusts, emulsifiable concentrates, flowable formulations, and the like. As solid carrier vehicles, such vegetable flours as soy bean flour and wheat flour, such ground minerals as diatomaceous earth, apetite, gypsum, talc, pyrophyllite and clay are used. As liquid diluent carriers, such inert organic liquids as kerosene, mineral oil, petroleum, solvent naphtha, xylene, cyclohexane, cyclohexanone, dimethylformamide, alcohol, and acetone, as well as water are employed. Conventional pesticidal surface-active agents including emulsifying agents and/or dispersing agents may be used when homogeneous and stable formulations are desired.

The concentration of the active ingredient in the pesticidal compositions may vary in accordance with types of the formulation, and it is settled generally at about 5 to 8 weight percent and preferably 20 to 80 weight percent for the wettable powder; 5 to 70 weight percent and preferably 10 to 50 weight percent for the emulsifiable concentrates; and 0.5 to 20 weight percent and preferably 1 to 10 weight percent for the dust formulation.

Wettable powders, emulsifiable concentrates and flowable formulations thus formulated are usually diluted with water to form the suspensions or emulsions, which are applied by spraying or drenching. Dusts and granules are applied directly.

Non-limiting examples of the insecticidal and acaricidal composition of the invention are as mentioned below:

EXAMPLE 10

Emulsifiable Concentrate

| | |
|---|---|
| Compound of this invention | 10 parts by weight |
| Dimethylformamide | 50 parts by weight |
| Xylene | 35 parts by weight |
| Alkylarylpolyoxyethylene ether | 5 parts by weight |

These are mixed together to provide an emulsifiable concentrate. It is diluted with water to an emulsion of the desired concentration.

EXAMPLE 11

Wettable Powder

| | |
|---|---|
| Compound of this invention | 20 parts by weight |
| Diatomaceous earth | 70 parts by weight |
| White carbon | 5 parts by weight |
| Sodium alkylsulfate | 5 parts by weight |

These are mixed and ground to provide homogeneous powders. It is diluted with water to a suspension of the desired concentration.

EXAMPLE 12

Dust Formulation

| | |
|---|---|
| Compound of this invention | 1 parts by weight |
| Talc | 98.6 parts by weight |
| Silicone | 0.3 parts by weight |
| Alkylarylpolyoxyethylene ether | 0.1 parts by weight |

These are mixed and pulverized to provide homogeneous fine powders.

EXAMPLE 13

Granular Formulation

| | |
|---|---|
| Compound of this invention | 5 parts by weight |
| Talc | 41.75 parts by weight |
| Diatomaceous earth | 41.75 parts by weight |
| Bentonite | 10 parts by weight |
| Sodium lignosulfate | 1.5 parts by weight |

These are mixed homogeneously and the mixture is granulated to granules having particle size of about 0.5 to 1 mm. The formulation is directly applied.

It is possible to use the compound of the present invention in a form of mixture with compounds having synergistic action on synthetic pyrethroids such as piperonyl butoxide, sulfoxide, safroxan and octachlorpropyl ether.

Use of the combinations of the compound of the present invention with other plant protection agents may provide insecticidal and acaricidal compositions which achieve results unattainable with separate compositions of the individual components. Other components with which the compound of the present invention can be used are, for example, as follows:

Pyrethroids:
  permethrin, cypermethrin, decamethrin, fenvalerate, fenpropanate, pyrethrins, allethrin, etc.

Organophosphorous insecticides:
  dichlorvos, malathion, fenitrothion, diazinon, fenthion, pyridafenthion, dimethoate, tetrachlovinphos, propaphs, acephate, salithion, etc.

Carbamate insecticides:
  BPMC, MTMC, MIPC, NAC, methomyl, cartap, etc.

Acaricides:
  BCPE, chlorobenzilate, chloropropylate, chlorophenamidine, amitraz, benzomate, dicofol, oyhexatin, polynaction, CPCBS, etc.

The unexpected superiority and outstanding activity of the novel compounds of the present invention is illustrated, without limitation by the following tests.

Test 1

Insecticidal activity extended to the green rice leafhopper (*Nephotettix cincticeps* Uhler)

A wettable powder formulated according to the above Example was diluted with water to the desired concentrations. A seedling of rice was immersed in the liquid formulation for 30 seconds and air-dried. The treated seedling was put in a test tube enclosing 10 female adults of the green rice leafhopper having resistances to organophosphorous insecticides and carbamate ones, and the opening of the test tube was capped with gauze. The test tube was placed in a room kept at 25° C. and 65% Relative Humidity and the degree of destruction was determined after 48 hours. Test results after a two times repetitions are shown in Table 2, wherein 100 percent means that all the insects were killed whereas 0 percent means none of the insects were killed.

TABLE 2

| | Degree of destruction (%) | | |
|---|---|---|---|
| | Concentration of active compound (ppm) | | |
| Compound No. | 31.3 | 7.8 | 2.0 |
| 2 | 100 | 95 | 50 |
| 3 | 100 | 95 | 80 |
| 4 | 100 | 100 | 100 |
| 6 | 100 | 100 | 100 |
| 8 | 100 | 100 | 95 |
| 10 | 100 | 100 | 100 |
| 11 | 100 | 70 | 60 |
| 12 | 100 | 100 | 100 |

TABLE 2-continued

| Compound No. | Degree of destruction (%) Concentration of active compound (ppm) | | |
|---|---|---|---|
| | 31.3 | 7.8 | 2.0 |
| 14 | 100 | 100 | 100 |
| 17 | 100 | 100 | 100 |
| 18 | 100 | 100 | 100 |
| 19 | 100 | 90 | 70 |
| 22 | | 100 | 100 |
| 24 | 100 | 100 | 95 |
| 26 | | 100 | 95 |
| 27 | | 100 | 100 |
| 28 | 100 | 100 | 80 |
| 29 | | 100 | 100 |
| 30 | | 100 | 100 |
| 31 | | 100 | 83 |
| 32 | | 100 | 100 |
| 34 | | 100 | 100 |
| 37 | | 100 | 90 |
| 38 | | 100 | 100 |
| 40 | | | 100 |
| 41 | | 100 | 90 |
| 43 | 100 | 80 | 50 |
| allethrin* | 100 | 45 | |
| fenvalerate** | 100 | 90 | 65 |

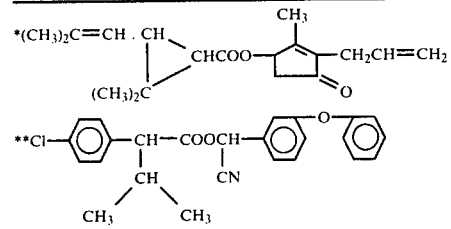

Test 2

Insecticidal activity extended to the armyworm (*Leucania separate Walker*)

An emulsifiable concentrate formulated according to the above Example was diluted with water to the desired concentrations. A leaf of corn was immersed in the liquid formulation for 30 seconds and air-dried. The treated leaf was put in a petri dish enclosing 5 third instar larvae of the armyworm, and the petri dish was capped with a sheet of glass. The petri dish was placed in a room kept at 25° C. and 65% Relative Humidity, and the degree of destruction was determined after 72 hours. Test results obtained under four times repetitions are shown in Table 3.

TABLE 3

| Compound No. | Degree of destruction (%) | Degree of ingestion hindrance* | Degree of destruction (%) | Degree of ingestion hindrance* |
|---|---|---|---|---|
| | Concentration of active compound (ppm) | | | |
| | 500 | | 125 | |
| 1 | 100 | ++ | 100 | ++ |
| 2 | 100 | +++ | 100 | ++ |
| 3 | 100 | ++ | 80 | ++ |
| 4 | 100 | ++ | 100 | ++ |
| 6 | 100 | ++ | 100 | ++ |
| 9 | 100 | ++ | 100 | ++ |
| 10 | 100 | ++ | 80 | ++ |
| 11 | 80 | ++ | 80 | ++ |
| 12 | 100 | ++ | 80 | ++ |
| 13 | 100 | ++ | 100 | ++ |
| 14 | 100 | ++ | 100 | ++ |
| 16 | 100 | ++ | 100 | ++ |
| 20 | 100 | ++ | 100 | ++ |
| 23 | 100 | ++ | 100 | ++ |
| 24 | 100 | ++ | 100 | ++ |
| 25 | 100 | ++ | 100 | ++ |

TABLE 3-continued

| Compound No. | Degree of destruction (%) | Degree of ingestion hindrance* | Degree of destruction (%) | Degree of ingestion hindrance* |
|---|---|---|---|---|
| | Concentration of active compound (ppm) | | | |
| | 500 | | 125 | |
| 26 | 100 | ++ | 100 | ++ |
| 27 | 100 | ++ | 100 | ++ |
| 29 | 100 | ++ | 100 | ++ |
| 30 | 100 | ++ | 100 | ++ |
| 31 | 100 | ++ | 100 | ++ |
| 32 | 100 | ++ | 100 | ++ |
| 33 | 100 | ++ | 100 | ++ |
| 34 | 100 | ++ | 100 | ++ |
| allethrin | 60 | ++ | 0 | + |
| fenvalerate | 100 | +++ | 100 | +++ |

*Hinderance in ingestion of the treated leaf of about 5 cm², wherein
+++ means hindered 100%,
++ means hindered 99-90,
+ means hindered 89-50 and
− means hindered 49-0.

Test 3

Insecticidal activity extended to the cotton aphid (*Aphis gossypii* Glover)

A wettable powder formulated according to the above Example was diluted with water to the desired concentrations. The liquid formulation was sprayed to a potted seedling of cucumber which was infested with the cotton aphid. The pot was placed in a room kept at 25° C. and 65% Relative Humidity, and the insecticidal activity was determined after 3 days. Test results obtained are shown in Table 4.

| Compound No. | Insecticidal activity* Concentration of active compound (ppm) | |
|---|---|---|
| | 125 | 31.3 |
| 2 | 10 | 9 |
| 4 | 10 | 9 |
| 6 | 10 | 10 |
| 9 | 9 | 8 |
| 10 | 10 | 10 |
| 12 | 10 | 8 |
| 13 | 10 | 10 |
| 14 | 10 | 10 |
| 17 | 10 | 10 |
| 18 | 10 | 8 |
| 22 | 10 | 10 |
| 24 | 10 | 9 |
| 26 | 10 | 10 |
| 27 | 10 | 8 |
| 29 | 10 | 10 |
| 30 | 10 | 10 |
| 33 | 10 | 10 |
| 34 | 10 | 10 |
| 36 | 10 | 10 |
| 37 | 10 | 6 |
| 38 | 10 | 7 |
| 40 | 10 | 9 |
| 42 | 9 | 8 |
| allethrin | 10 | 6 |

| *Insecticidal activity | Degree of destruction (%) |
|---|---|
| 10 | 100 |
| 9 | 99-90 |
| 8 | 89-80 |
| 7 | 79-70 |
| 6 | 69-60 |

Test 4

Insecticidal activity extended to the northern house mosquito (*Culex pipiens molestus Forskal*).

An emulsifiable concentrate formulated according to the above Example was diluted with water to the concentration of 1 ppm. Into 150 ml of the liquid formulation put in a 200 ml beaker, 10 third instar larvae of the northern house mosquito were released. The beaker was placed in a room ketp at 25° C. and 65% Relative Humidity, and the degree of destruction was determined after 7 days. Test results obtained under two times repetition are shown in Table 5.

TABLE 5

| Compound No. | Degree of destruction (%) |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 13 | 100 |
| 14 | 100 |
| 21 | 100 |
| 24 | 100 |
| 26 | 100 |
| 29 | 100 |
| 30 | 100 |
| 32 | 100 |
| 33 | 100 |
| 34 | 100 |
| 36 | 100 |
| 37 | 100 |
| 40 | 100 |
| 43 | 100 |
| 44 | 100 |
| allethrin | 100 |
| fenvalerate | 100 |

Test 5

Accaricidal activity extended to the desert spider mite (*Tetranychus destertorum Banks*)

On the first true leaves of potted kidney bean plants were inoculated 30 female adults of the desert spider mite, and wounded mites were removed from the plant after 1 day. An emulsifiable concentrate formulated according to the above Example was diluted with water to the concentration of 500 ppm. The liquid formulation was sprayed on the plant, and the mortality of adult mite was investigated after 3 days. Test results obtained are shown in Table 6.

TABLE 6

| Compound No. | Adult mortality |
|---|---|
| 1 | +++* |
| 2 | +++ |
| 3 | +++ |
| 4 | +++ |
| 6 | +++ |
| 9 | +++ |
| 10 | +++ |
| 11 | +++ |
| 12 | +++ |
| 13 | +++ |
| 14 | +++ |
| 17 | +++ |
| 19 | +++ |
| 20 | +++ |
| 26 | +++ |
| 34 | +++ |
| 40 | +++ |
| allethrin | — |
| fenvalerate | +++ |

| *Rating | % |
|---|---|
| +++ | 100 |
| ++ | 80–99 |
| + | 50–79 |
| — | 0–49 |

Test 6

Toxicity to carp (*Cyprinus carpio*)

The compound of the present invention was suspended in water containing a small amount of Tween-80, and prepared water samples having varied concentration of the compound ranging from 0.01 to 10 ppm. To each 5 l of the water kept at 20° C., 5 larvae of carp (about 5 cm length and 2.5 g weight on the average) were released, and the median tolerance limit (TLm) determined based on the mortality at 48 hours afterwards. Results obtained are shown in Table 7.

TABLE 7

| Compound No. | TLm (48 hours) (ppm) |
|---|---|
| 2 | >0.5 |
| 4 | 0.5–2 |
| 8 | >0.5 |
| 9 | >0.5 |
| 10 | >10 |
| 11 | >0.5 |
| 12 | >0.5 |
| 17 | >10 |
| 18 | >10 |
| 21 | >0.5 |
| 22 | >0.5 |
| 23 | >0.5 |
| 24 | >0.5 |
| 27 | >0.5 |
| 29 | >0.5 |
| 30 | >0.5 |
| 31 | >0.5 |
| 32 | >0.5 |
| 33 | >0.5 |
| 34 | >0.5 |
| 35 | >0.5 |
| 37 | >0.5 |
| 38 | >0.5 |
| 39 | >0.5 |
| 40 | >0.5 |
| 41 | >0.5 |
| allethrin | 0.01–0.05 |
| fenvalerate | <0.01 |

We claim:

1. A compound of the formula

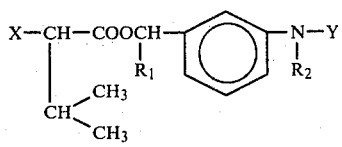

wherein
X is phenyl substituted with halogen, lower alkyl, lower haloalkyl, lower halalkoxy, 3,4-methylenedioxy or nitro group, naphthyl, styryl or lower alkenyl substituted with chlorine,
$R_1$ is hydrogen, cyano or ethynyl,
$R_2$ is hydrogen, lower alkyl, lower alkenyl or lower alkynyl, and Y is phenyl or halophenyl.

2. A compound according to claim 1, wherein Y is 4-chlorophenyl.

3. A compound according to claim 1, wherein X is 4-chlorophenyl, $R_1$ is hydrogen or cyano, $R_2$ is hydrogen or methyl and Y is halophenyl.

4. A compound according to claim 3, $R_2$ is methyl.

5. A compound according to claim 3, $R_2$ is hydrogen.

6. An insecticidal and acaricidal composition comprising an inert carrier and an effective amount of a compound of claim 1.

7. An insecticidal and acaricidal composition comprising an inert carrier and an effective amount of a compound of claim 2.

8. An insecticidal and acaricidal composition comprising an inert carrier and an effective amount of a compound of claim 3.

9. An insecticidal and acaricidal composition comprising an inert carrier and an effective amount of a compound of claim 4.

10. An insecticidal and acaricidal composition comprising an inert carrier and an effective amount of a compound of claim 5.

* * * * *